United States Patent [19]
Ariagno

[11] Patent Number: 6,016,816
[45] Date of Patent: Jan. 25, 2000

[54] MULTI-COLORED DENTAL FLOSS AND METHOD OF MAKING

[75] Inventor: Joseph L. Ariagno, Long Sault, Canada

[73] Assignee: Seaway Yarns Limited, Cornwall, Canada

[21] Appl. No.: 09/354,737

[22] Filed: Jul. 16, 1999

[51] Int. Cl.[7] ..................................... A61C 15/00
[52] U.S. Cl. ............................................. 132/321
[58] Field of Search ..................... 132/321, 200

[56] References Cited

U.S. PATENT DOCUMENTS

| | | |
|---|---|---|
| 3,897,796 | 8/1975 | Erickson .................. 132/321 |
| 4,941,487 | 7/1990 | VanBeneden ............. 132/321 |
| 5,365,874 | 11/1994 | Dorfman .................. 132/321 |
| 5,526,831 | 6/1996 | Gillian et al. ............ 132/321 |
| 5,692,530 | 12/1997 | Bible et al. .............. 132/321 |

*Primary Examiner*—Todd E. Manahan
*Attorney, Agent, or Firm*—Harold C. Baker

[57] ABSTRACT

A process for making a multi-colored dental floss formed of a plurality of bundles of fibers comprising; knitting said floss into a tube shape, flattening said tube, printing both surfaces of said flattened tube with a sequence of colored stripes, and unknitting said floss.

6 Claims, 2 Drawing Sheets

MULTI-COLORED DENTAL FLOSS AND METHOD OF MAKING

FIELD OF THE INVENTION

The present invention relates to a multi-colored dental floss, and in particular to such a floss having a plurality of colors seriatim in the floss, such colors repeating at intervals throughout the length of the floss.

BACKGROUND OF THE INVENTION

Striped dental floss has been well known in which the floss consists of a multiplicity of strands with one or more colored strands twisted with strands colored white, producing a striped floss with the colored strand contrasting with the "non-colored" or white strands. Dental floss has also been produced in which plural bundles of fibers have been "texturized" and impregnated with chemotherapeutic agents, see for example, U.S. Pat. No. 5,711,935, granted Jan. 27, 1998, to Hill et al. U.S. Pat. No. 3,897,796 dated Aug. 5, 1975, to Erickson teaches a dental floss having color coded sections that are approximately one half inch long, indicating waxed and unwaxed sections of the floss. The waxed sections are blue in color, and the unwaxed portions are white. No teaching as to how the color is added to the floss is contained in the patent.

SUMMARY OF THE INVENTION

The present invention provides a multi-colored floss and a method for producing it which makes possible the heretofore impossible production of a floss having all fibers dyed with a repetitively recurring sequence of colors extending the length of the floss. Thus for example, the color sequence might be red, yellow, blue, green, orange, and white repeated continuously at variously lengths throughout the length of the floss.

In accordance with the process of the present invention, a floss consisting of a plurality of bundles of fibers is knit into a tubular shape, the tubular knit product is then flattened and space dyed, or printed on each side with a sequence of colored stripes, and the knitted tubular shape is then unknitted (unraveled), and wound under tension to form the completed floss. The floss may then be cut into lengths and packaged in suitable dispensers for consumers. In the course of knitting the tube, a desirable crimp is also imparted to the floss. The unknitted floss is colored in a continuously varying range of colors as a result of the above process. It will be appreciated by those practicing the invention that the length of each color in the floss can be varied by changing the width of the colored stripes printed on the flattened tube. It will also be appreciated that the color sequence can be change by altering the registration of the of the printing on opposite sides of the knitted flattened tube. Necessarily the dyes used in printing must be food grade dyes, for example those approved by the U.S. Food and Drug Administration. Such dyes are available in a full range of colors.

Dental floss is normally made from Nylon™ fibers, and special steps must be taken to ensure that the fibers are permanently colored by the food dyes. In accordance with another aspect of the invention, special procedures for dyeing the floss are described.

It will be appreciated by those skilled in the art of Nylon processing that a lubricant is required for further processing the dyed floss. Such lubricating material must be also FDA approved for use with food, And have excellent anti-static properties, without changing the color of the floss and must be easily scourable.

BRIEF DESCRIPTION OF THE DRAWINGS

Referring to the accompanying drawings.

DETAILED DESCRIPTION OF THE PREFERRED EMBODIMENTS

Figure 1:
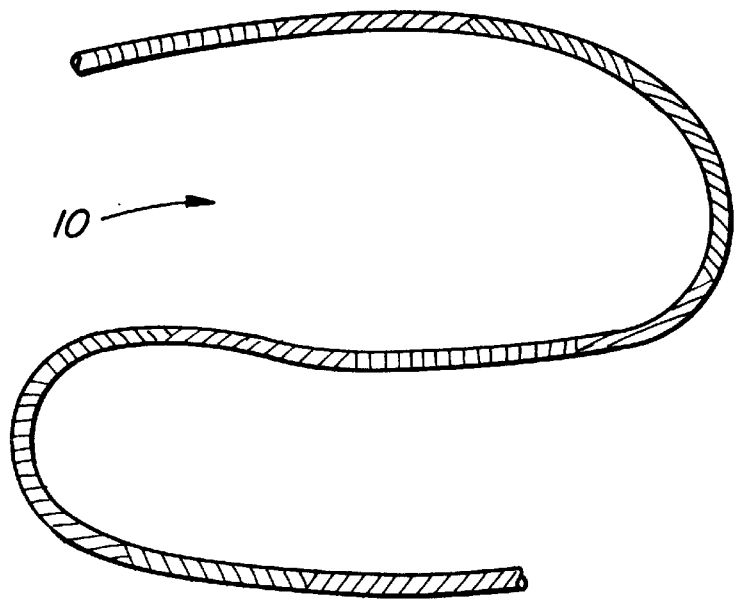
FIG. 1 is a general view of a length of floss in accordance with the present invention.

FIG. 1 is an illustration of the multi-colored floss made in accordance with the process of the present invention showing a plurality of different colored portions spaced along the length of the floss. The floss 10 is formed of a plurality of bundles of Nylon fibers twisted or commingled together in the usual way to form a dental floss, which then undergoes treatment in accordance with the process of the invention to become multi-colored.

Figure 2:
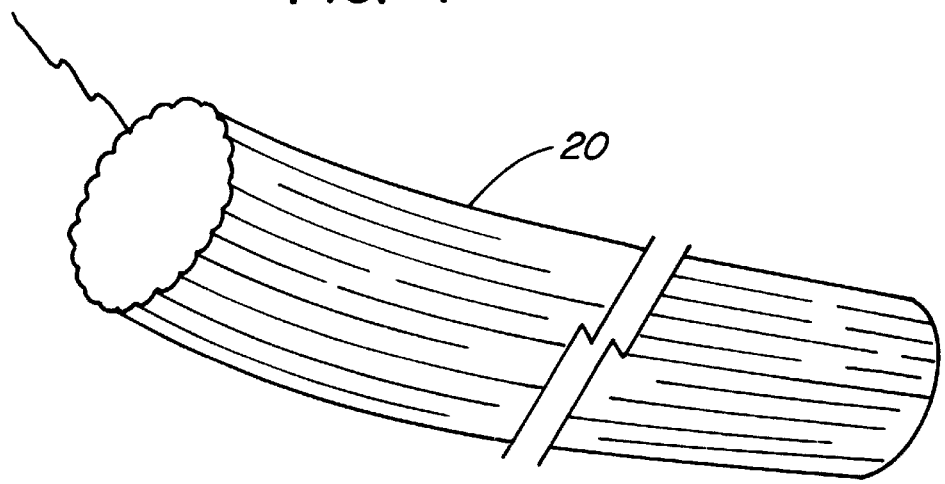
FIG. 2 is a perspective view of the knit tube of undyed floss.

FIG. 2 illustrates the untreated fiber knitted into a tube 20 of considerable length, typically containing tens of thousands of feet of untreated floss. This tube 20 is then flattened to form a basically two sided linear shape of narrow transverse dimension and considerable length.

Figure 3:
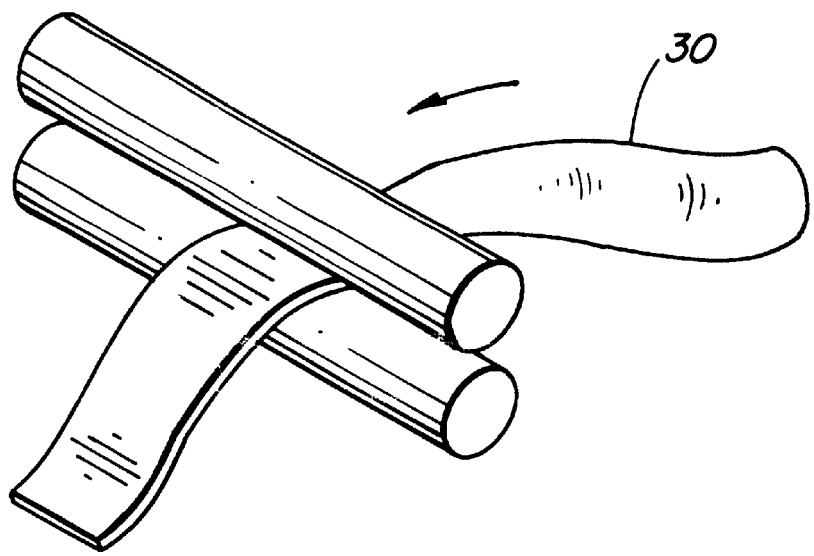
FIG. 3 is a view of the flattened knitted tube passing through suitable printing rolls.
Figure 5:
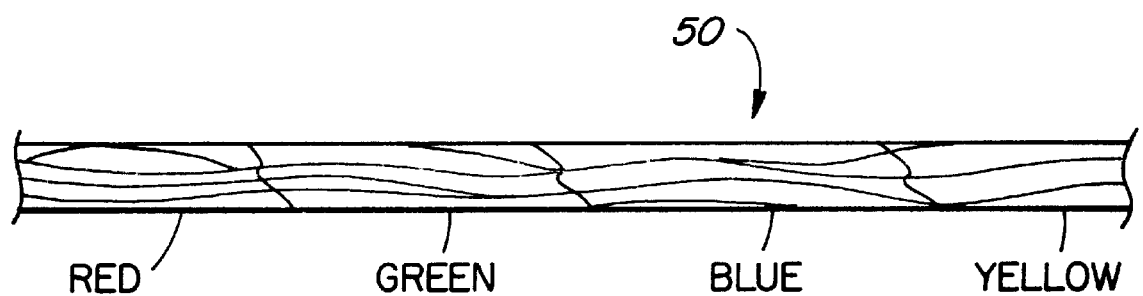
FIG. 5 illustrates a length of multi-colored floss after unknitting the tube.

The flattened tube 30, as shown in FIG. 3 is the passed through printing rolls and printed or space dyed first on one surface and then on the opposite surface. The registration between the printing on opposite surfaces of the flattened tube may be adjusted to create different sequences of color along the floss after it is unknitted.

Figure 4:
FIG. 4 is a plan view of the printed flattened tube after printing, and before unknitting.

FIG. 4 shows the flattened tube with the color sequence printed on one face of the tube 40. The printing on the opposite face will be similar.

Further processing of the floss comprises unknitting the tube, under tension and winding on a spool. Finally the floss is cut into suitable lengths and packaged in dispensers for consumer use.

Suitable dyes for creating the multi-colored floss are Food Grade, as approved by the U.S. Food and Drug Administration(FDA). Such dyes include but are not limited to Warner Jenkinson 05601 FD&C Blue#1, D2541 U.S. Purple, FDC.Red#3, 06503 FD&C Green#3, and K7059° D&C Yellow#10. To these food grade dyes may be added antiwick powder sold by Tri-Tex Co. Inc. of St. Eustache Quebec, to control the viscosity of the dye, and an anti-static lubricant, such as Syntholube G from TriTex co. inc. The pH of the dye solutions needs to be adjusted to stay in the range of approximately 3, with Citric acid, which is approved by the U.S. FDA, to ensure that the floss is permanently dyed, and the color does not wash out of the floss. Such pH adjustment is made by adding citric acid to the dye formulation. At a pH of 3 the dye strikes best and the color fastness is obtained by steaming the floss at approximately 213° F. post to impregnation of dye and chemicals. Steaming time is dependant on depth of shade, but should be no less than 5–6 minutes. Steaming also sterilizes the floss.

Colors are applied by passing the knitted material through several engraved printing rolls, so that both sides are printed, as discussed above. Engraving is designed and the configuration of the rolls is designed to not overlap the colors, other than by design.

What is claimed is:

1. A process for making a multi-colored dental floss formed of a plurality of bundles of fibers comprising; knitting said floss into a tube shape, flattening said tube, printing both surfaces of said flattened tube with a sequence of colored stripes, and unknitting said floss.

2. A process as defined in claim 1, in which said floss is made of Nylon and said printing step is carried out using dyes that are approved for food, and said dyes are adapted to not wash off said floss.

3. A process as claimed in claim 2 in which the knitted floss is dyed in a printing process wherein the dye is maintained at a pH of approximately 3.

4. A process as claimed in claim 3 which the floss is steamed at a temperature of approximately 213° F. for a time of no less than five minutes.

5. A process as claimed in claim 1 wherein said printing is done with engraved printing rolls, and both sides of the knitted tube are printed, with the colors not overlapping.

6. A multi-colored dental floss having more than two colors sequentially dyed into said floss throughout the length thereof.

* * * * *